(12) United States Patent
Gao et al.

(10) Patent No.: US 10,443,378 B2
(45) Date of Patent: Oct. 15, 2019

(54) APPARATUS AND METHOD FOR DOWNHOLE IN-SITU DETERMINATION OF FLUID VISCOSITY

(71) Applicant: Halliburton Energy Services, Inc., Houston, TX (US)

(72) Inventors: Li Gao, Katy, TX (US); Wei Zhang, Houston, TX (US); Michael T. Pelletier, Houston, TX (US); Christopher Michael Jones, Houston, TX (US); Dingding Chen, Tomball, TX (US); David Earl Ball, Meadows Place, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 15/926,506

(22) Filed: Mar. 20, 2018

(65) Prior Publication Data

US 2018/0209268 A1    Jul. 26, 2018

Related U.S. Application Data

(63) Continuation-in-part of application No. 14/419,435, filed as application No. PCT/US2012/053488 on Aug. 31, 2012, now abandoned.

(51) Int. Cl.
*E21B 49/08* (2006.01)
*G01N 11/16* (2006.01)
(Continued)

(52) U.S. Cl.
CPC .............. *E21B 49/08* (2013.01); *E21B 47/10* (2013.01); *G01N 11/14* (2013.01); *G01N 11/162* (2013.01);
(Continued)

(58) Field of Classification Search
CPC ....... E21B 49/08; E21B 47/10; G01N 11/162; G01N 27/74; G01N 11/14; G01N 2011/147; G01N 2203/0676
(Continued)

(56) References Cited

U.S. PATENT DOCUMENTS

| 2,603,087 A | 7/1952 | Von Hortenau |
| 2,607,217 A | 8/1952 | Merten et al. |

(Continued)

FOREIGN PATENT DOCUMENTS

| WO | WO 86/00408 | * | 1/1986 |
| WO | WO 2011/063994 A1 | | 6/2011 |

OTHER PUBLICATIONS

English machine translation for document WO 8600408.*

(Continued)

*Primary Examiner* — Daniel S Larkin
*Assistant Examiner* — Anthony W Megna Fuentes
(74) *Attorney, Agent, or Firm* — Haynes and Boone, LLP

(57) ABSTRACT

An apparatus to determine fluid viscosities downhole in real-time includes a housing and an excitation element positioned therein. Electrical circuitry provides a drive signal that excites an excitation element into rotational oscillations. A detector produces a response signal correlating to the detected oscillating movement of the excitation element. Circuitry onboard the apparatus utilizes the drive and response signals to determine the fluid viscosity.

17 Claims, 5 Drawing Sheets

(51) Int. Cl.
 *E21B 47/10* (2012.01)
 *G01N 27/74* (2006.01)
 *G01N 11/14* (2006.01)

(52) U.S. Cl.
 CPC ........ *G01N 27/74* (2013.01); *E21B 2049/085* (2013.01); *G01N 2011/147* (2013.01); *G01N 2203/0676* (2013.01)

(58) Field of Classification Search
 USPC ................................. 73/54.01–54.43, 152.18
 See application file for complete search history.

(56) References Cited

U.S. PATENT DOCUMENTS

| | | | |
|---|---|---|---|
| 4,724,385 | A | 2/1988 | Vail |
| 4,864,849 | A | 9/1989 | Wright |
| 5,698,773 | A | 12/1997 | Blom et al. |
| 6,581,476 | B1 | 6/2003 | Fremerey |
| 6,584,833 | B1 | 7/2003 | Jamison et al. |
| 2002/0040592 | A1* | 4/2002 | Getman ................ G01N 9/002 73/54.25 |
| 2002/0140425 | A1* | 10/2002 | Prammer ............. G01R 33/307 324/303 |
| 2002/0178803 | A1 | 12/2002 | Pelletier et al. |
| 2003/0019622 | A1 | 1/2003 | Goodson et al. |
| 2003/0033859 | A1 | 2/2003 | Schoeb et al. |
| 2003/0233868 | A1 | 12/2003 | Rieder et al. |
| 2010/0152524 | A1 | 6/2010 | Sentmanat |
| 2011/0146975 | A1 | 6/2011 | O'Malley et al. |
| 2012/0085161 | A1 | 4/2012 | Kumar |
| 2012/0227483 | A1* | 9/2012 | Kruspe ............... E21B 47/0002 73/152.55 |
| 2015/0160111 | A1* | 6/2015 | Lewis ................ G01N 11/162 73/54.41 |

OTHER PUBLICATIONS

Extended European Search Report, EP 12883512.1, dated Feb. 11, 2016, 6 pages.

International Search Report and The Written Opinion of the International Searching Authority, or the Declaration, dated Nov. 23, 2012, PCT/US2012/053488, 8 pages, International Searching Authority, US.

\* cited by examiner

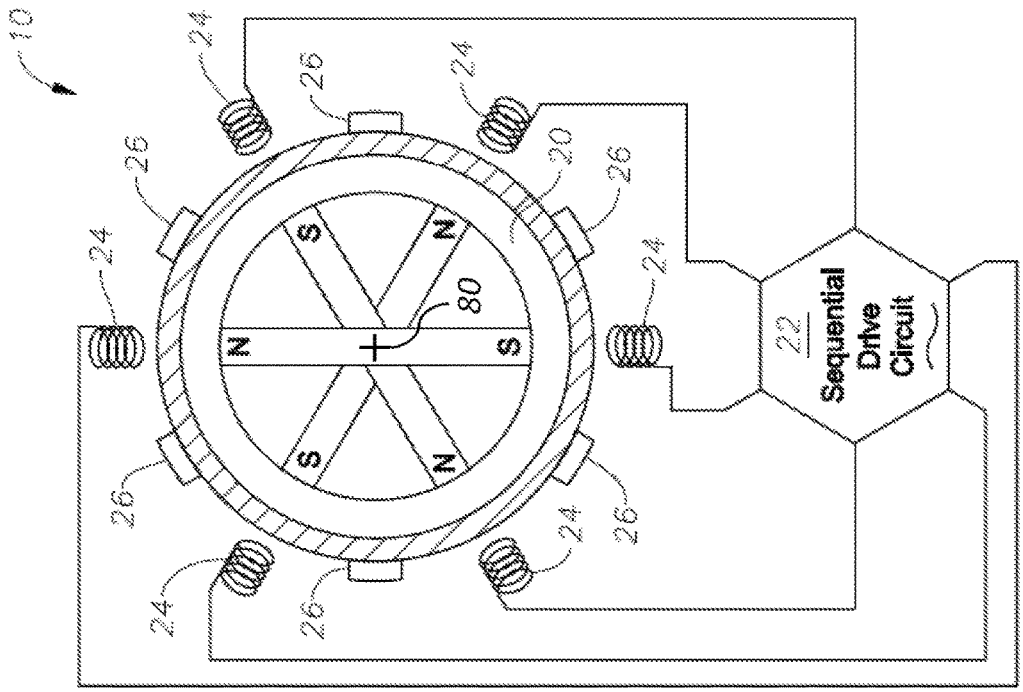
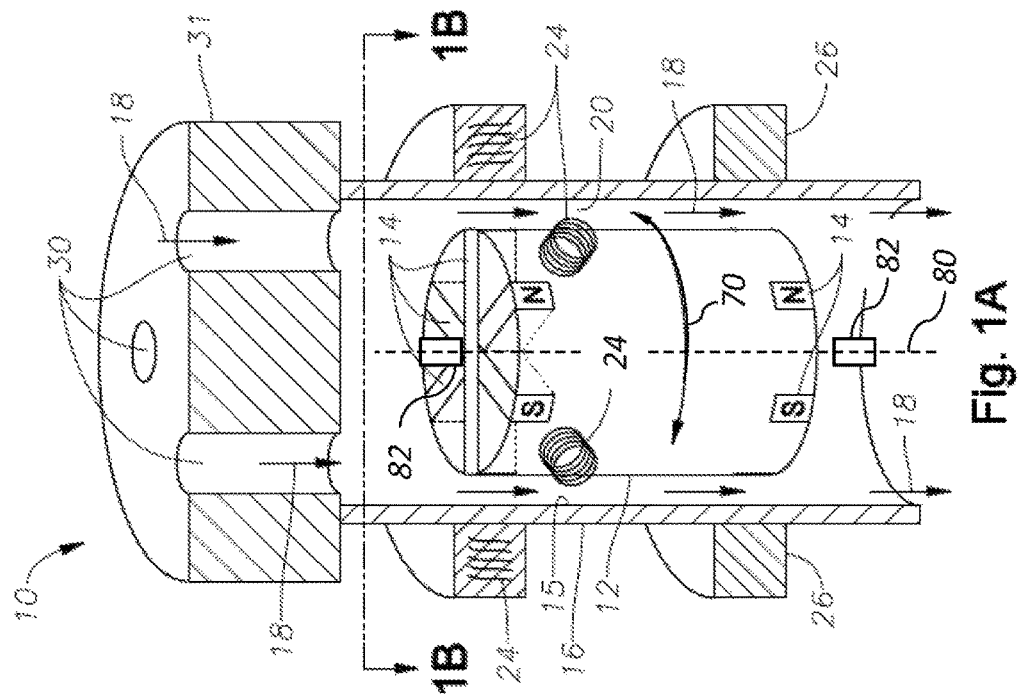

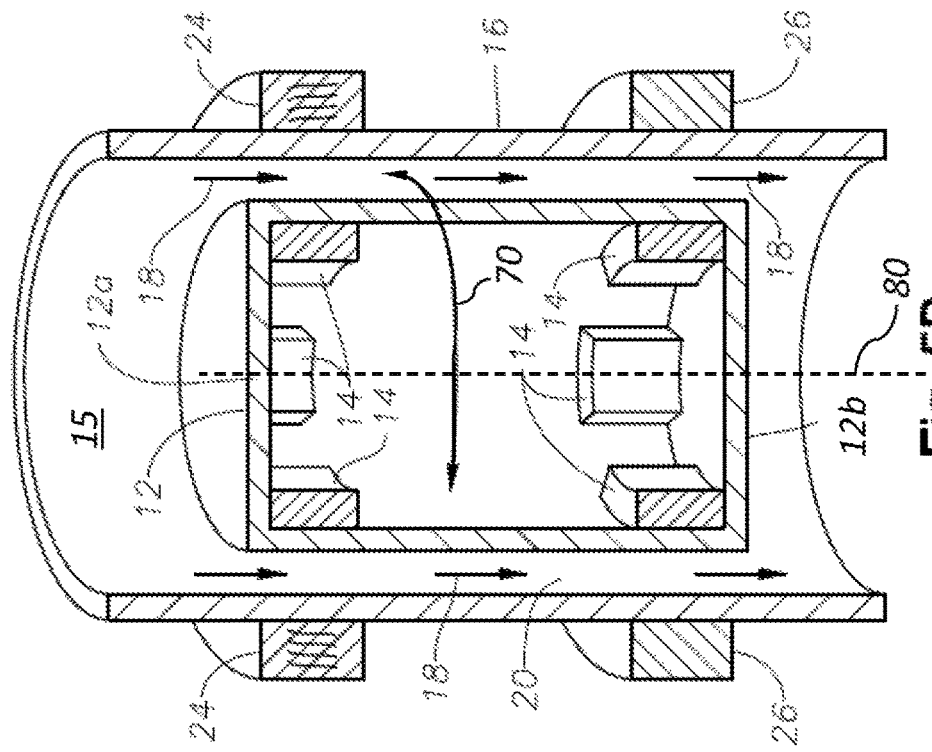
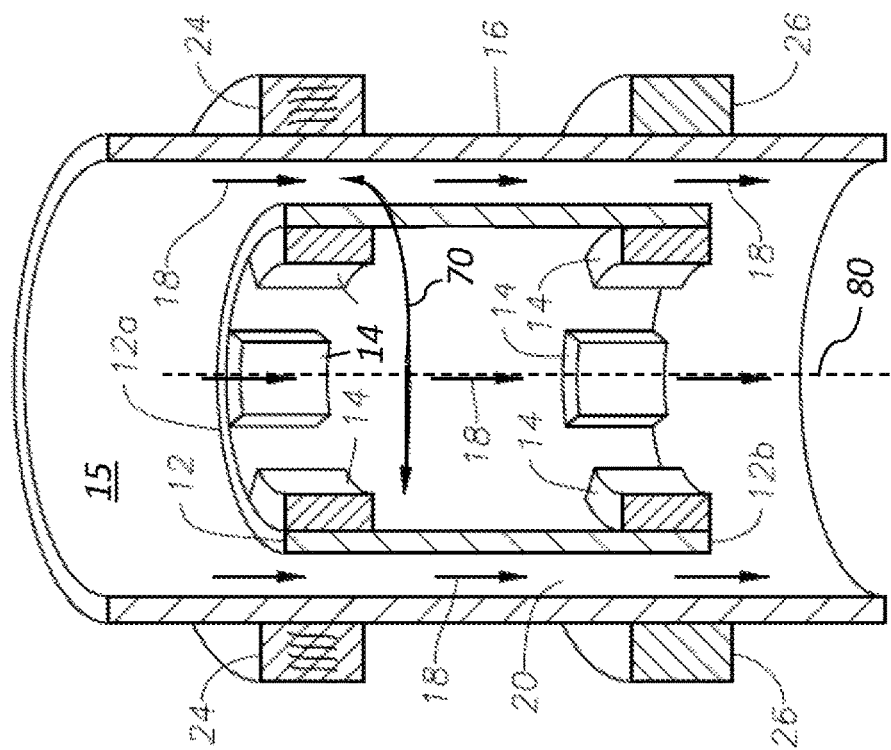

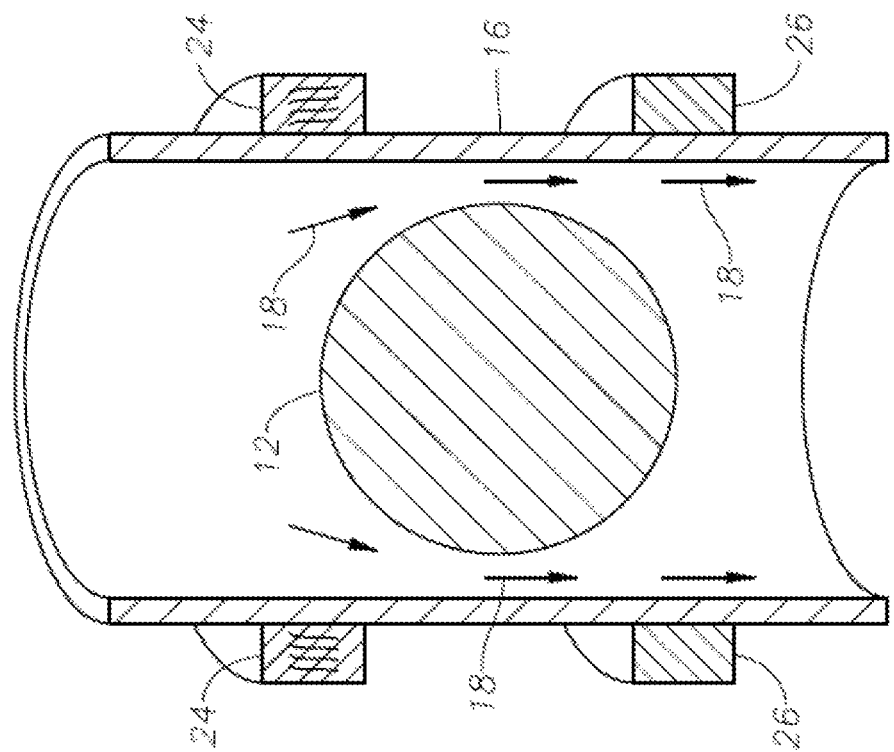
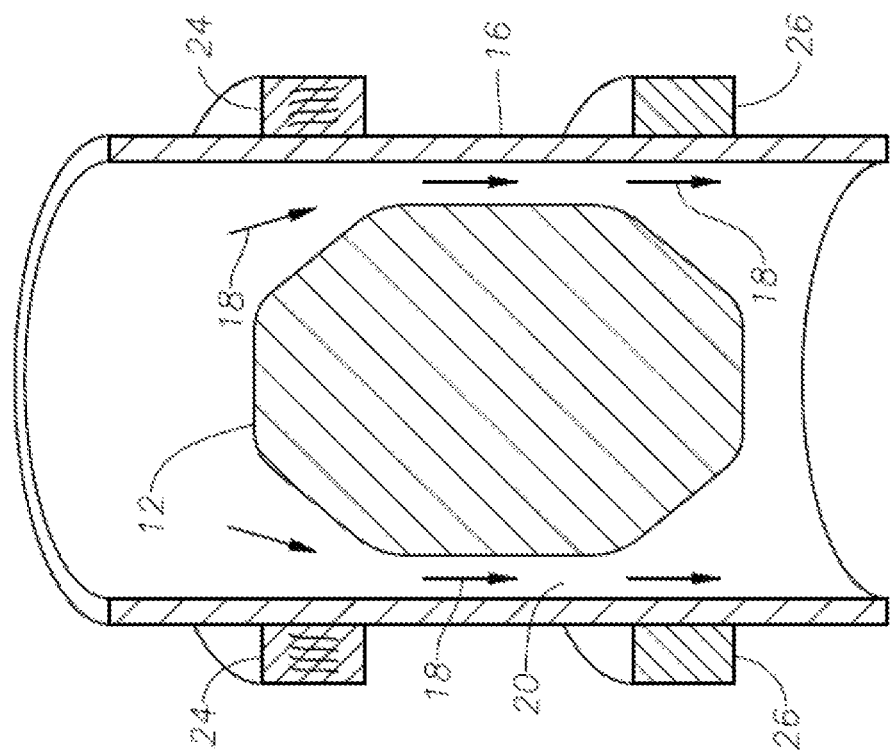

APPARATUS AND METHOD FOR DOWNHOLE IN-SITU DETERMINATION OF FLUID VISCOSITY

CROSS-REFERENCE TO RELATED APPLICATION

The present application is a continuation-in-part of U.S. application Ser. No. 14/419,435 filed on 3 Feb. 2015, which claims priority to PCT International Patent Application No. PCT/US0212/053488, filed on 31 Aug. 2012. The entire disclosures of these prior applications are incorporated herein by this reference.

FIELD OF THE INVENTION

The present invention generally relates to fluid viscosity measurements and, more particularly, to downhole in-situ measurement of reservoir fluid viscosity.

BACKGROUND

Conventionally, instruments utilized to measure fluid viscosity in downhole environments utilize sensors based on vibrating wires or tuning forks, which are both known to be adversely affected by flow regime and the presence of fluid inhomogeneities. Moreover, such sensors are only sensitive to a small fluid volume in close proximity to the wire or fork.

Accordingly, in view of the these disadvantages, there is a need in the art for a viscosity measurement device which can provide accurate, downhole, real-time, viscosity measurements regardless of the presence of fluid inhomogeneities.

BRIEF DESCRIPTION OF THE DRAWINGS

FIGS. 1A & 1B illustrate cross-sectional views of a rotationally oscillating viscosity measurement apparatus according to an exemplary embodiment of the present invention;

FIGS. 5A-5D illustrate cross-sectional views of the excitation element according to various alternative exemplary embodiments of the present invention.

DETAILED DESCRIPTION OF THE DISCLOSURE

Figure 3:
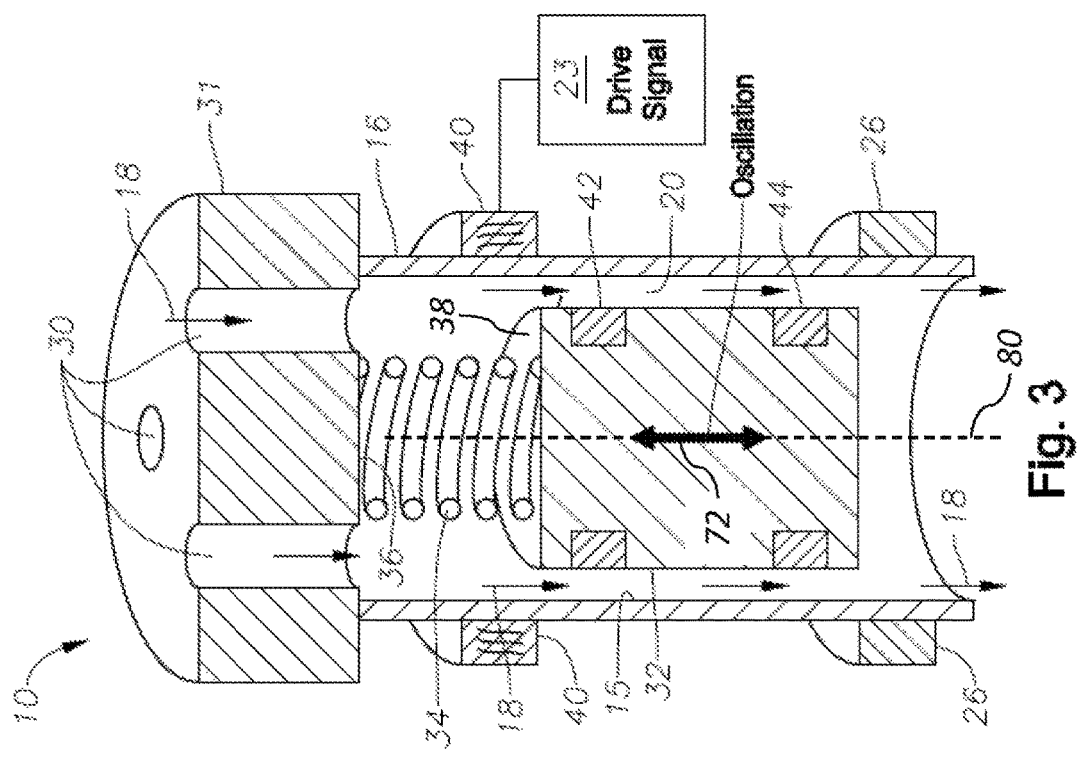
FIG. 3 illustrates a cross-sectional view of an axially oscillating viscosity measurement apparatus according to an alternative exemplary embodiment of the present invention.

Illustrative embodiments and related methodologies of the present invention are described below as they might be employed in an apparatus and method for in-situ determination of fluid viscosity. In the interest of clarity, not all features of an actual implementation or methodology are described in this specification. In addition, the "exemplary" embodiments described herein refer to examples of the disclosed invention. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methodologies of the invention will become apparent from consideration of the following description and drawings.

FIGS. 1A & 1B illustrate a viscosity measurement apparatus ("VMA") 10 according to an exemplary embodiment of the present invention. The exemplary embodiments of VMA 10 disclosed herein are hermitically sealed in a high temperature and high pressure housing for use in downhole environments. Those ordinarily skilled in the art having the benefit of this disclosure realize a variety of non-magnetic, corrosion resistant materials may be used to construct VMA 10 such as, for example, non-magnetic stainless steel.

VMA 10 includes a non-magnetic housing 16 having a bore 15 therethrough. At one end of non-magnetic housing 16 is a cap 31 having a plurality of bores 30 therethrough in which fluid flows. An excitation element 12 which, in this exemplary embodiment, is a rotator that rotates about a central axis 80 of the rotator 12, includes a series of radially arranged magnets 14 at its upper and lower ends, and is positioned inside bore 15. As shown, rotator 12 is a solid cylindrical element. However, the rotator 12 can also be a hollow cylinder with capped or open ends as seen in FIGS. 5A and 5B, as well as other shapes, such as those shown in FIGS. 5C and 5D. Magnets 14 are positioned within rotator 12 at its upper and lower ends, with each magnet's magnetic moment aligned along the axis 80 which is perpendicular to the flow direction, as illustrated in FIG. 1B. Arrows 18 denote the direction of fluid flow through VMA 10. As such, rotator 12 is positioned inside housing 16 as part of the flow line, thus creating an annular flow area 20 between rotator 12 and housing 16.

One or more retaining structures 82 can be utilized to retain rotator 12 inside housing 16. The retaining structure(s) may be, for example, magnets 82 placed above and below rotator 12 such that the opposing forces between rotator 12 and the magnets act to retain rotator 12. Also, a mechanical retainer, such as a needle, may be utilized as the retaining structure 82. Ordinarily skilled persons having the benefit of this disclosure realize there are a variety of ways in which to retain rotator 12 inside non-magnetic housing 16 while still allowing maximum fluid through VMA 10.

Further referring to the exemplary embodiment of FIGS. 1A & 1B, a sequential drive circuit 22 is utilized to drive rotator 12 into a rotational oscillation (see arrows 70). If rotator 12 were driven into rotation such that the rotator spins, similar to a rotator in a pump, then turbulence and perturbations may be imparted into the fluid being measured thereby negatively impacting the measurements taken by the VMA 10. Some of the impacts can be that the viscosity of the fluid is changed by shear forces induced in the fluid by rotation of the rotator 12. Additionally, if features protrude from a surface of the rotator 12, such as a rotator of a pump with fins, the turbulence and perturbations imparted into the fluid can be further increased, leading to uncertainty in shear stress in a fluid, thereby increasing the negative impacts to the fluid measurements, particularly for non-newtonian fluids, leading to both reduction in a sensitivity of the measurement tool and an increase in measurement uncertainty of the rotator 12 to fluid characteristics such as viscosity. Driving the rotator 12 into rotational oscillations (arrows 70) can minimize turbulence and perturbations imparted to the fluid being measured and more accurate measurement data of the fluid can be collected. Non-newtonian fluids are often encountered in hydrocarbon exploration. A continuously rotating element can impart shear into the fluid. Depending on whether the fluid is shear-thinning, or shear-thickening, the introduction of shear into the measuring device may change the characteristics of the fluid (such as viscosity), leading to errors in measurements of the fluid characteristics. Therefore, it is beneficial to apply small amplitude oscillations, such as the rotational oscillations described herein, instead of a spinning rotation (e.g. a rotor in a fluid pump) to minimize the shear effects in the fluid and improve the accuracy of the measurements of the fluid characteristics.

Circuit 22 includes all necessary processing and storage capability to calculate and store viscosity measurements. Once calculated, the viscosity readings may be stored onboard VMA 10 or transmitted to the surface via any suitable wired or wireless transmission methodology. Circuit 22 may be powered by an on-tool power supply such as, for example, a battery which may be converted to AC power using any suitable DC to AC converters. In the alternative, however, power may be supplied to circuit 22 via a wireline (not shown) or a DC power source. Also, in this exemplary embodiment, circuit 22 is located onboard housing 16. However, those of ordinary skill in the art having the benefit of this disclosure realize that circuit 22 may also be located remotely from VMA 10.

In this exemplary embodiment, a series of coils 24 are radially arranged proximate to upper magnets 14 along non-magnetic housing 16 such that a phase-delayed sinusoidal AC current is delivered to coils 24 sequentially varying with time. As a result, rotator 12 is driven to rotationally oscillate (arrows 70) within the VMA 10. As used herein, "rotational oscillation" refers to a rotation of, for example, the rotator 12, such that the rotator 12 rotates less than a full revolution (i.e. a partial rotation) in one direction, then rotates less than a full revolution (i.e. a partial rotation) in an opposite direction, and repeats the partial rotations in the opposite directions to create the rotational oscillations (i.e. partially rotated back and forth). A degree of rotation can be determined by the placement of the coils 24. Detectors 26 are placed radially around housing 16, in order to detect the rotational oscillations of the rotator 12. Detectors 26 may be any variety of detectors such as, for example, simple coils, Hall sensors, magneto-resistive sensors such as GMR sensors, etc., as would be understood by one ordinarily skilled in the art having the benefit of this disclosure.

During operation of exemplary embodiments of the present invention, VMA 10 is deployed downhole during a wireline pumpout formation test, logging while drilling ("LWD") formation test, measured while drilling ("MWD") formation test, or other wireline operations. Furthermore, persons ordinarily skilled in the art having the benefit of this disclosure realize the VMA 10 may be deployed downhole as a stand-alone unit or as otherwise desired. Once located downhole at the desired position, fluid is pumped (or otherwise flows) through housing 16 as shown in FIG. 1A (fluid flow identified by arrow 18). Sequential drive circuit 22 is then powered up via the wireline or an onboard power supply, and coils 24 impart partial rotations in opposite directions to rotator 12. As fluid flows into housing 16, around rotator 12, and through annular flow area 20, the fluid's viscosity imparts a drag on the rotational oscillations of rotator 12. As will be described below, detectors 26 sense the electromagnetic signal emitted from rotationally oscillating lower magnets 14, produce a signal in response to the emitted signal (i.e., response signal) and, based upon this response signal, VMA 10 is utilized to determine the viscosity of the fluid flowing through annular flow area 20.

Figure 2:
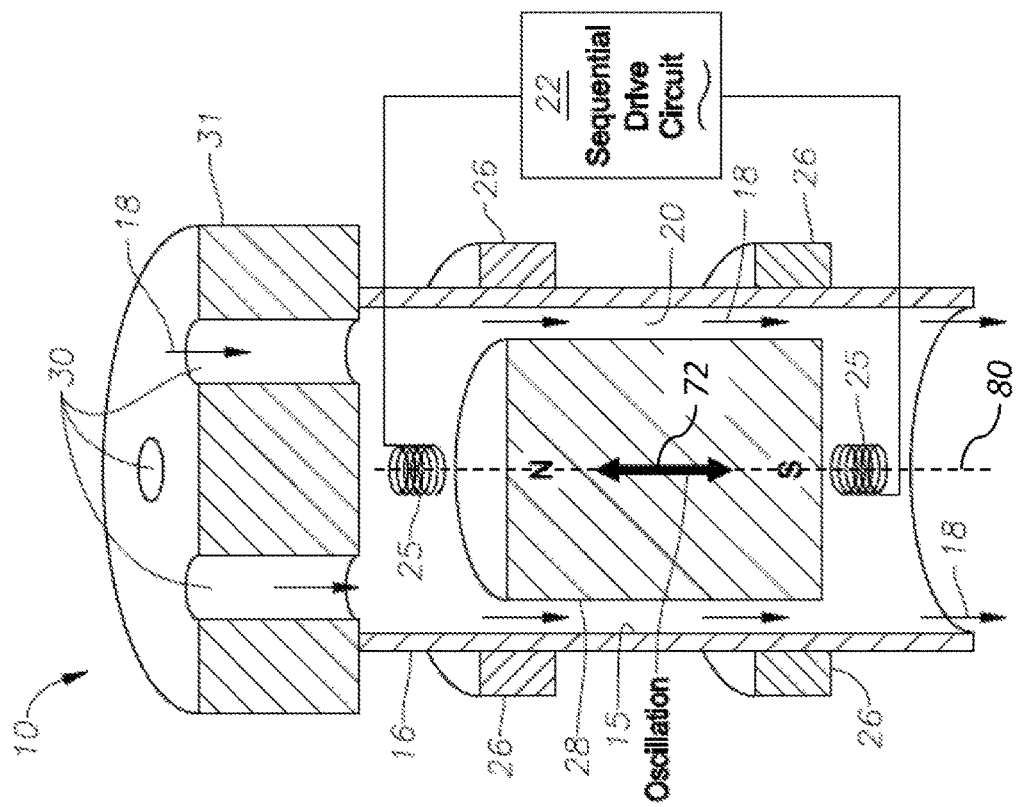
FIG. 2 illustrates a cross-sectional view of an axially oscillating viscosity measurement apparatus according to an alternative exemplary embodiment of the present invention.

FIG. 2 illustrates VMA 10 according to an alternative exemplary embodiment of the present invention. VMA 10 consists of a non-magnetic housing 16 having a bore 15 in which an excitation element 28 is positioned. VMA 10 also includes a series of bores 30 extending through cap 31 at the upper end of housing 16, thus forming the fluid flow channel along arrows 18. In this exemplary embodiment, excitation element 28 is an oscillating permanent magnetic element that oscillates axially as indicated by arrows 72. The oscillating permanent magnetic element having its magnetic moment aligned along its axis 80 in a direction parallel to the flow direction 18. As such, an annular flow area 20 is created between excitation element 28 and housing 16. Detectors 26 are located outside housing 16 and are placed above and below excitation element 28, as shown. As previously described, detectors 26 may be any variety of detectors as understood in the art.

A retaining structure (not shown) may be provided to ensure excitation element 28 remains in the section of housing 16 between detectors 26. For example, magnets having opposing poles can be placed above and below the oscillating excitation element 28 or mechanical stoppers may be used (as indicated in FIG. 1A by retainer 82). Accordingly, those ordinarily skilled in the art having the benefit of this disclosure realize there are a variety of structures to retain the element between the detectors. In this exemplary embodiment, first and second drive coils 25 are placed along the inner diameter of housing 16 along the flow area above and below excitation element 28. As in the previous embodiment, sinusoidal AC drive current is fed sequentially into first and second coils 25 in order to drive excitation element 28 into axial oscillation indicated by arrows 72.

During operation of this exemplary embodiment of the present invention, VMA 10 of FIG. 2 is deployed downhole using any desired methodology. Once downhole, fluid is pumped (or otherwise flows) through non-magnetic housing 16 as shown in FIG. 2 (fluid flow identified by arrow 18). A sequential drive signal is provided by circuit 22 to power first and second coils 25, thus forcing excitation element 28 into axial oscillations (arrow 72). As fluid flows into housing 16, around excitation element 28, and through annular flow area 20, the fluid's viscosity imparts a drag on the axial oscillations of excitation element 28. As will be described below, detectors 26 sense the electromagnetic signals emitted from the opposing magnetic poles of excitation element 28 and, based upon this response signal, VMA 10 is utilized to determine the viscosity of the fluid flowing through annular flow area 20.

FIG. 3 illustrates VMA 10 according to yet another alternative exemplary embodiment of the present invention. VMA 10 includes a non-metallic housing 16 having a series of bores 30 extending through cap 31 coupled to housing 16, thus forming the fluid flow channel along arrows 18 as in previous embodiments. An excitation element 32 is positioned inside non-magnetic housing 16 along the fluid flow channel, thus forming annular flow area 20 between the excitation element 32 and housing 16. In this exemplary embodiment, excitation element 32 is an oscillating element which oscillates along an axis 80 that is parallel to an axis of bore 15. A spring 34 is positioned between the lower end of surface 36 of cap 31 and the upper surface 38 of oscillating element 32. Spring 34 is utilized to both maintain excitation of and retain oscillating element 32 inside non-magnetic housing 16. A coil 40 is placed around housing 16 adjacent to the upper end of oscillating element 32, while a detector 26 is placed adjacent a lower end of oscillating element 32. As previously described, detector 26 may comprise a variety of sensors.

Oscillating element 32 comprises upper magnet 42 which is used to excite oscillation of element 32 when current is supplied to coil 40. A lower magnet 44 is also included in element 32 in order to supply the electromagnetic signal that is sensed by detector 26. Thus, during operation, fluid flows through bores 30, around oscillating element 32, and through annular flow area 20. Drive signal 23 is supplied to coil 40 which, in turn, induces movement of upper magnet 42 that results in oscillation of element 32. Drive signal 23 may be supplied by circuit 22, a step input, or some other suitable current source. Drive signal 23 and the spring constant of spring 34 work together to maintain the oscillation of element 32. However, the viscosity of the fluid acts as a drag on the oscillation of element 32. At the same time, detector 26 senses the electromagnetic signal emitted by lower magnet 44. This measurement can be made on resonant frequency, decay, or start-up time constant, which are related to fluid viscosity as would be readily understood by one ordinarily skilled in the art having the benefit of this disclosure. As in previous embodiments, detector 26 produces a response signal based upon the measured signal emitted by magnet 44, which is then used to determine the viscosity of the fluid passing through annular flow area 20.

Figure 4A:
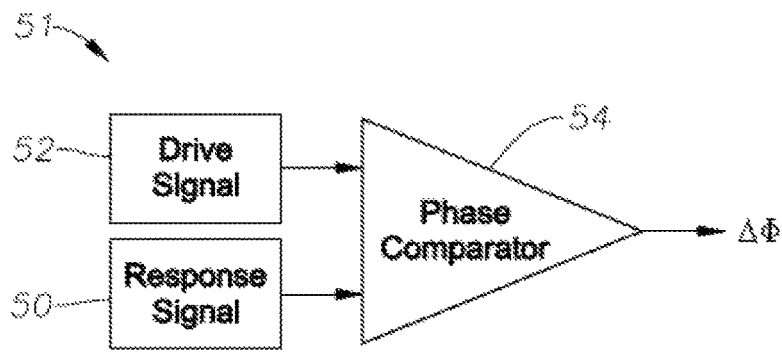
FIG. 4A illustrates a block diagram of a phase comparator circuit according to an exemplary embodiment of the present invention.
Figure 4B:
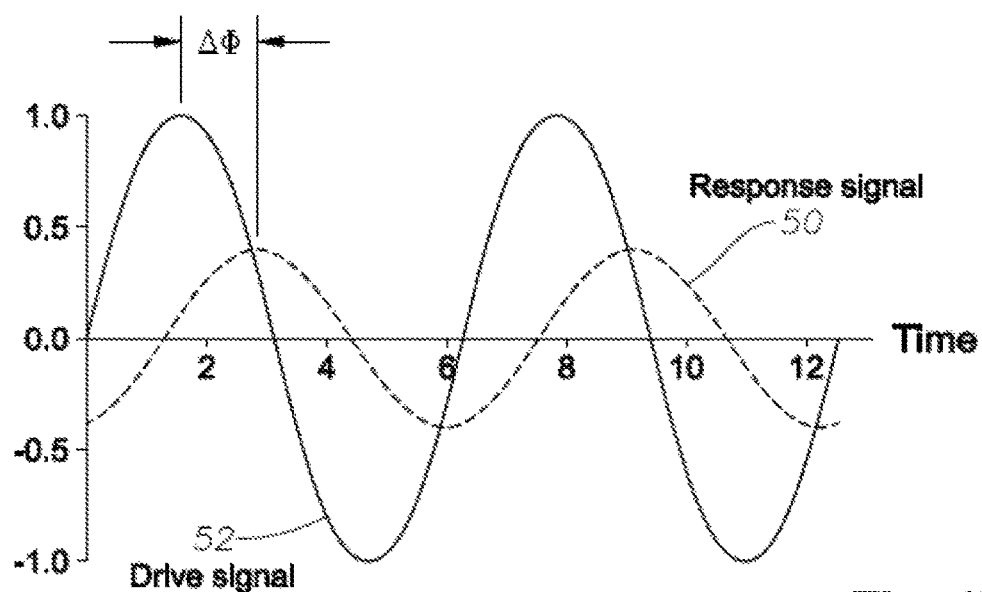
FIGS. 4B & 4C are graphical illustrations of delta phase and its correlation to fluid viscosity according to an exemplary embodiment of the present invention.
Figure 4C:
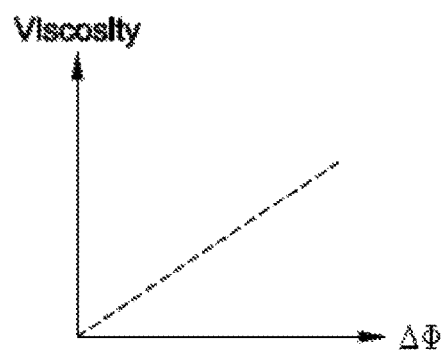

The determination of the fluid viscosity will now be described. In one exemplary embodiment of the present invention, detectors 26 of each embodiment described herein detect the motion of the rotator 12 or elements 28, 32, and the resultant data is fed into a phase comparator circuit. FIGS. 4A-4C illustrates a phase comparator circuit 51 and its operation according to exemplary embodiments of the present invention. Phase comparator circuit 51, like sequential drive circuit 22, comprises all components necessary for processing, analyzing, and storage of viscosity data, and may form part of sequential drive circuit 22. Thus, circuit 51 may be located on VMA 10 or located remotely such as, for example, on the wireline, other tools, or the surface. Phase comparator circuit 51 also comprises an analysis unit (not shown) having a database containing the delta phase delays for known viscosities, one or more controllers/sensing circuitry to control operation of the circuit and detectors 26, as well as a communications unit to communicate the viscosity data via wired or wireless means. Moreover, VMA 10 may be supervised and controlled via a remote peripheral device as would be understood by one ordinarily skilled in the art having the benefit of this disclosure.

In FIG. 4A, response signal 50, received from detectors 26, and the original drive signal 52 (used to excite movement of the rotator or elements) are fed into phase comparator 54. The resultant output is delta phase ("$\Delta\Phi$"), which refers to the phase difference between original drive signal 52 and response signal 50. A graphical representation of $\Delta\Phi$ is illustrated in FIG. 4B, which plots drive signal 52 and response signal 50 along amplitude/time coordinates.

Referring to FIG. 4C, those ordinarily skilled in the art having the benefit of this disclosure understand it is well-known that the phase angle correlates with the viscosity of fluid. Thus, as illustrated in FIG. 4C, as $\Delta\Phi$ increases, the fluid viscosity also increases. $\Delta\Phi$ may then be calibrated using viscosity standards at the desired temperatures and pressures. Thereafter, circuit 51 calibrates the $\Delta\Phi$ data and encodes it into wireline logging software or LWD or MWD data to provide real time, in-situ viscosity measurement during the pump process.

In addition, $\Delta\Phi$ can be used to modify the pump out procedure in real-time, taking into consideration such reservoir parameters as hydraulic pressure, draw down pressure, fluid contamination, etc., as determined by viscosity as well as other means. As would be understood by persons ordinarily skilled in the art having the benefit of this disclosure, multiple reservoir parameters can be estimated from formation testing by fitting an analytical or numerical model with sequentially measured drawdown and buildup pressures. Because of multi-parameter interaction in a flow model, any means which helps minimize the number of unknowns through direct and robust measurements would be useful to reduce the uncertainty of formation evaluation. Given the fluid mobility, for example, accurate viscosity measurement will help determination of reservoir permeability. Reservoir permeability and formation porosity also can be evaluated from the resistivity, nuclear and acoustic logging tools. Moreover, with the advanced data integration technology available today, it is possible to simplify the formation tester data interpretation by resolving the minimized number of unknowns through inverse analysis.

Although not illustrated, VMA 10 may be deployed downhole utilizing a variety of methodologies such as, for example, in conjunction with MWD or LWD operations. In an exemplary embodiment of the present invention, VMA 10 comprises a part of a formation testing tool deployed via a wireline which provides for electrical coupling and bi-directional data communication. The formation testing tool may also include, for example, modules to handle electrical/hydraulic power conversion, fluid sample storage, data recordation, flow control, telemetry, etc., as would be readily understood by persons ordinarily skilled in the art having the benefit of this disclosure. Moreover, VMA 10 may further include an on-board CPU to monitor and control operation of VMA 10 during sampling operations, or a surface control unit could be utilized to accomplish the same, or some combination of the two.

The exemplary embodiments of the present invention may be altered in a variety of ways. For example, in the embodiments of FIGS. 1A & 1B, rotator 12 may be hollowed and open at both ends, thus forming a hollow tube, with magnets 14 being coupled to the inner diameter of the hollow tube. In this way, as rotator 12 rotationally oscillates, fluid will flow both through rotator 12 and around rotator 12 via annular flow area 20 (FIG. 5A). In addition, if rotator 12 were sealed at ends 12a, 12b, it may be hollowed, thus decreasing/minimizing its weight in order to reduce the power requirement necessary to excite its movement (FIG. 5B). Also, rotator 12 may comprise a conical (FIG. 5C) or spherical (FIG. 5D) shape to reduce the possibility of particulates in the fluid becoming jammed inside non-magnetic housing 16. Those ordinarily skilled in the art having the benefit of this disclosure realize these and other features may be combined and/or applied to the other embodiments disclosed herein as well. For example, any of the features and/or alterations mentioned above may be combined or included in the embodiments depicted in FIGS. 1A, 1B, 2, and 3. For example, the spring 34 in FIG. 3 can be used as a retainer in FIGS. 1A, 2 and 5B. In FIG. 2, the spring 34 can have the coil 25 placed within the spring, or around the spring to drive the element 28. For example, the rotator 12 of FIG. 1A can be substituted for the elements in FIGS. 3, 5B. For example, the rotators 12 in FIGS. 5A-5D can be substituted for the rotator 12 in FIG. 1A, as well as substituted for the elements in FIGS. 2 and 3.

Moreover, other forms of circuitry could be utilized in place of phase comparator 51 to determine the fluid viscosity. For example, in the exemplary embodiment of FIGS. 1A & 1B, the torque required to rotationally oscillate the rotator 12 during fluid flow can be correlated to determine fluid viscosity. In the exemplary embodiments utilizing oscillating elements, the displacement of the oscillating element in one or both directions can also be correlated to determine fluid viscosity. Furthermore, in an alternative embodiment of FIG. 3, element 32 may be excited by the flow of the fluid through bores 30 instead of coil 40. In such an embodiment, the fluid viscosity could be determined based on a correlation of the vertical displacement of element 32 which would be detected by detector 26. Moreover, an amplitude or frequency comparator circuit could be utilized in place of the phase comparator in order to determine the characteristic differences of the drive and response signals. Accordingly, those ordinarily skilled in the art having the benefit of this disclosure realize these and a variety of other viscosity deterministic models can be utilized in the present invention.

One general aspect includes an apparatus to determine a viscosity of a fluid, the apparatus including: a non-magnetic housing having a bore extending therethrough; a magnetic excitation element positioned within the bore, thereby forming a flow area between the excitation element and a housing in which fluid to be measured can flow; at least one coil positioned adjacent to the magnetic excitation element to provide a drive signal to excite the magnetic excitation element into rotational oscillations; at least one detector positioned adjacent to the magnetic excitation element, the at least one detector being disposed to produce a response signal based upon the rotational oscillations of the magnetic excitation element; and circuitry which utilizes the drive signal and the response signal to determine the viscosity of the fluid being measured.

Implementations may include one or more of the following features. The apparatus where the magnetic excitation element is a rotator that rotates on an axis parallel to an axis of the bore. The apparatus where the viscosity of the fluid is determined based on a phase difference between the drive signal and the response signal. The apparatus where the housing is non-magnetic and the excitation element is magnetic. The apparatus further including at least one coil positioned adjacent to the excitation element in order to excite the excitation element into the rotational oscillations. The apparatus where the excitation element is a rotator that rotates on an axis parallel to an axis of the bore. The apparatus where the excitation element is a hollow cylinder with one or more magnets disposed on an inner surface of the excitation element.

The apparatus further including circuitry that determines the fluid viscosity based upon the response signal. The apparatus further including a retaining structure to retain the excitation element within the bore. The apparatus further including a cap coupled at the first end of the housing, the cap including a plurality of bores through which the fluid can flow. The apparatus further including a spring coupled between the excitation element and the cap.

A method where determining the viscosity of the fluid flowing through the flow area further includes utilizing circuitry onboard the tool to determine the viscosity of the fluid. The method where driving the rotational oscillations further includes initiating rotation of the excitation element on an axis parallel to the axis of the housing, and producing a response signal based upon the rotational oscillations of the excitation element further includes producing the response signal based upon the rotation of the excitation element.

The method where determining the viscosity of the fluid flowing through the flow area includes: comparing a drive signal to the response signal; determining at least one characteristic difference of the drive and response signals; and determining the viscosity of the fluid based upon the at least one characteristic difference of the drive and response signals. The method where the at least one characteristic difference includes a phase difference between the drive signal and the response signal. The method where deploying the tool downhole includes deploying the tool during a logging while drilling, measurement while drilling or a wireline operation. The method where determining the viscosity of the fluid flowing through the flow area includes determining the viscosity of the fluid in real-time. The method where determining the viscosity of the fluid flowing through the flow area further includes modifying a downhole operation in real-time based upon the viscosity of the fluid.

Another general aspect includes an apparatus to determine a viscosity of a fluid, the apparatus including: a housing having a first end, a second end opposite the first end, and a bore extending between the first and second ends; an excitation element positioned within the bore, thereby forming a flow area between the excitation element and the housing in which fluid to be measured can flow; and a detector positioned adjacent to the excitation element to produce a response signal based upon rotational oscillations of the excitation element, where the response signal is dependent upon the fluid viscosity.

Implementations may include one or more of the following features. The apparatus where the housing is non-magnetic and the excitation element is magnetic. The apparatus further including at least one coil positioned adjacent to the excitation element in order to excite the excitation element into the rotational oscillations. The apparatus where the excitation element is a rotator that rotates on an axis parallel to an axis of the bore. The apparatus where the excitation element is a hollow cylinder with one or more magnets disposed on an inner surface of the excitation element. The apparatus further including circuitry that determines the fluid viscosity based upon the response signal. The apparatus further including a retaining structure to retain the excitation element within the bore. The apparatus further including a cap coupled at the first end of the housing, the cap including a plurality of bores through which the fluid can flow. The apparatus further including a spring coupled between the excitation element and the cap.

The method where determining the viscosity of the fluid flowing through the flow area further includes utilizing circuitry onboard the tool to determine the viscosity of the fluid. The method where driving the rotational oscillations further includes initiating rotation of the excitation element on an axis parallel to the axis of the housing, and producing a response signal based upon the rotational oscillations of the excitation element further includes producing the response signal based upon the rotation of the excitation element. The method where determining the viscosity of the fluid flowing through the flow area includes: comparing a drive signal to the response signal; determining at least one characteristic difference of the drive and response signals; and determining the viscosity of the fluid based upon the at least one characteristic difference of the drive and response signals.

The method where the at least one characteristic difference includes a phase difference between the drive signal and the response signal. The method where deploying the tool downhole includes deploying the tool during a logging while drilling, measurement while drilling or a wireline operation. The method where determining the viscosity of the fluid flowing through the flow area includes determining the viscosity of the fluid in real-time. The method where determining the viscosity of the fluid flowing through the flow area further includes modifying a down-hole operation in real-time based upon the viscosity of the fluid.

Yet another general aspect includes a method to determine a viscosity of a fluid in a downhole environment, the method including: deploying a tool downhole; allowing the fluid to flow through a flow area of the tool, the flow area being positioned between a housing and an excitation element of the tool; driving the excitation element into rotational oscillations; producing a response signal based upon the rotational oscillations of the excitation element; and determining the viscosity of the fluid flowing through the flow area based upon the response signal.

Implementations may include one or more of the following features. The method where determining the viscosity of the fluid flowing through the flow area further includes utilizing circuitry onboard the tool to determine the viscosity of the fluid. The method where driving the rotational oscillations further includes initiating rotation of the excitation element on an axis parallel to the axis of the housing, and producing a response signal based upon the rotational oscillations of the excitation element further includes producing the response signal based upon the rotation of the excitation element. The method where determining the viscosity of the fluid flowing through the flow area includes: comparing a drive signal to the response signal; determining at least one characteristic difference of the drive and response signals; and determining the viscosity of the fluid based upon the at least one characteristic difference of the drive and response signals.

The method where the at least one characteristic difference includes a phase difference between the drive signal and the response signal. The method where deploying the tool downhole includes deploying the tool during a logging while drilling, measurement while drilling or a wireline operation. The method where determining the viscosity of the fluid flowing through the flow area includes determining the viscosity of the fluid in real-time. The method where determining the viscosity of the fluid flowing through the flow area further includes modifying a down-hole operation in real-time based upon the viscosity of the fluid.

The foregoing disclosure may repeat reference numerals and/or letters in the various examples. This repetition is for the purpose of simplicity and clarity and does not in itself dictate a relationship between the various embodiments and/or configurations discussed. Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the apparatus in use or operation in addition to the orientation depicted in the figures. For example, if the apparatus in the figures is turned over, elements described as being "below" or "beneath" other elements or features would then be oriented "above" the other elements or features. Thus, the exemplary term "below" can encompass both an orientation of above and below. The apparatus may be otherwise oriented (rotated 90 degrees or at other orientations) and the spatially relative descriptors used herein may likewise be interpreted accordingly.

Although various embodiments and methodologies have been shown and described, the invention is not limited to such embodiments and methodologies and will be understood to include all modifications and variations as would be apparent to one skilled in the art. Therefore, it should be understood that the invention is not intended to be limited to the particular forms disclosed. Rather, the intention is to cover all modifications, equivalents and alternatives falling within the spirit and scope of the invention as defined by the appended claims.

The invention claimed is:

1. An apparatus to determine a viscosity of a fluid, the apparatus comprising:
   a non-magnetic housing having a bore extending therethrough;
   a magnetic excitation element positioned within the bore, thereby forming a flow area between the excitation element and a housing in which fluid to be measured can flow;
   at least one coil positioned adjacent to the magnetic excitation element to provide a drive signal to excite the magnetic excitation element into rotational oscillations;
   at least one detector positioned adjacent to the magnetic excitation element, the at least one detector being disposed to produce a response signal based upon the rotational oscillations of the magnetic excitation element; and
   circuitry which utilizes the drive signal and the response signal to determine the viscosity of the fluid being measured.

2. The apparatus of claim 1, wherein the magnetic excitation element is a rotator that rotates on an axis parallel to an axis of the bore.

3. The apparatus of claim 1, wherein the viscosity of the fluid is determined based on a phase difference between the drive signal and the response signal.

4. An apparatus to determine a viscosity of a fluid, the apparatus comprising: a housing having a first end, a second end opposite the first end, and a bore extending between the first and second ends; an excitation element positioned within the bore, thereby forming a flow area between the excitation element and the housing in which fluid to be measured can flow; at least one coil positioned adjacent to the excitation element to provide a drive signal to excite the excitation element into rotational oscillations; a detector positioned adjacent to the excitation element to produce a response signal based upon the rotational oscillations of the excitation element, wherein the response signal is dependent upon the fluid viscosity; and circuitry that determines the fluid viscosity based upon the response signal and the drive signal.

5. The apparatus of claim 4, wherein the housing is non-magnetic and the excitation element is magnetic.

6. The apparatus of claim 4, wherein the excitation element is a rotator that rotates on an axis parallel to an axis of the bore.

7. The apparatus of claim 4, wherein the excitation element is a hollow cylinder with one or more magnets disposed on an inner surface of the excitation element.

8. The apparatus of claim 4, further comprising a retaining structure to retain the excitation element within the bore.

9. The apparatus of claim 4, further comprising a cap coupled at the first end of the housing, the cap comprising a plurality of bores through which the fluid can flow.

10. A method to determine a viscosity of a fluid in a downhole environment, the method comprising: deploying a tool downhole; allowing the fluid to flow through a flow area of the tool, the flow area being positioned between a housing and an excitation element of the tool; driving the excitation element into rotational oscillations by utilizing a drive signal; producing a response signal based upon the rotational oscillations of the excitation element; and determining the viscosity of the fluid flowing through the flow area based upon the response signal and the drive signal.

11. The method of claim 10, wherein determining the viscosity of the fluid flowing through the flow area further comprises utilizing circuitry onboard the tool to determine the viscosity of the fluid.

12. The method of claim 10, wherein driving the rotational oscillations further comprises initiating rotation of the excitation element on an axis parallel to the axis of the housing, and producing the response signal based upon the rotational oscillations of the excitation element further comprises producing the response signal based upon the rotation of the excitation element.

13. The method of claim 10, wherein determining the viscosity of the fluid flowing through the flow area comprises: comparing the drive signal to the response signal; determining at least one characteristic difference of the drive and response signals; and determining the viscosity of the fluid based upon the at least one characteristic difference of the drive and response signals.

14. The method of claim 13, wherein the at least one characteristic difference comprises a phase difference between the drive signal and the response signal.

15. The method of claim 10, wherein deploying the tool downhole comprises deploying the tool during a logging while drilling, measurement while drilling or a wireline operation.

16. The method of claim 10, wherein determining the viscosity of the fluid flowing through the flow area comprises determining the viscosity of the fluid in real-time.

17. The method of claim 10, wherein determining the viscosity of the fluid flowing through the flow area further comprises modifying a down-hole operation in real-time based upon the viscosity of the fluid.

* * * * *